United States Patent
Xu et al.

(10) Patent No.: US 9,458,070 B2
(45) Date of Patent: Oct. 4, 2016

(54) 1, 3, 3, 3-TETRAFLUOROPROPENE PREPARATION PROCESS

(71) Applicants: SINOCHEM MODERN ENVIRONMENTAL PROTECTION CHEMICALS (XI'AN) CO., LTD., Xi'an, Shaanxi (CN); Sinochem Lantian Co., Ltd., Zhejiang (CN)

(72) Inventors: Lei Xu, Shaanxi (CN); Gang Yang, Shaanxi (CN); Huie Yang, Shaanxi (CN); Shukang Chen, Shaanxi (CN); Zhixia Zhao, Shaanxi (CN)

(73) Assignees: SINOCHEM MODERN ENVIRONMENTAL PROTECTION CHEMICALS (XI'AN) CO., LTD., Shaanxi (CN); Sinochem Lantian Co., Ltd., Zhejiang (CN)

( * ) Notice: Subject to any disclaimer, the term of this patent is extended or adjusted under 35 U.S.C. 154(b) by 0 days.

(21) Appl. No.: 14/653,510

(22) PCT Filed: Dec. 17, 2013

(86) PCT No.: PCT/CN2013/089633
§ 371 (c)(1),
(2) Date: Jun. 18, 2015

(87) PCT Pub. No.: WO2014/094587
PCT Pub. Date: Jun. 26, 2014

(65) Prior Publication Data
US 2015/0307420 A1    Oct. 29, 2015

(30) Foreign Application Priority Data
Dec. 19, 2012 (CN) ........................ 2012 1 0554563

(51) Int. Cl.
C07C 17/25     (2006.01)
C07C 17/383    (2006.01)
C07C 17/20     (2006.01)

(52) U.S. Cl.
CPC ............. *C07C 17/25* (2013.01); *C07C 17/206* (2013.01); *C07C 17/383* (2013.01)

(58) Field of Classification Search
CPC .... C07C 17/25; C07C 17/206; C07C 17/383
See application file for complete search history.

(56) References Cited

U.S. PATENT DOCUMENTS 8,293,954 B2 * 10/2012 Merkel ................... C07C 17/25
570/156
2012/0059200 A1 * 3/2012 Pokrovski ............. C01B 7/0706
570/156

FOREIGN PATENT DOCUMENTS

| CN | 102164881 A | 8/2011 |
| CN | 102351637 A | 2/2012 |
| CN | 102351637 B | * 10/2013 |
| EP | 2341040 A1 | 7/2011 |

OTHER PUBLICATIONS

CN 102351637 B, Oct. 2013, pp. 1-6; English translation.*
CN102164881, Aug. 24, 2011, pp. 1-18; English translation.*
CN102351637, Feb. 15, 2012, pp. 1-6; English translation.*
Extended European Search Report issued in corresponding EP Application No. 13865346.4 mailed Jun. 28, 2016 (5 pages).
Office Action issued Jun. 28, 2016 in corresponding Japanese application No. 2015-548171 (w/translation) (4 pages).

* cited by examiner

*Primary Examiner* — Jafar Parsa
*Assistant Examiner* — Medhanit Bahta
(74) *Attorney, Agent, or Firm* — Osha Liang LLP

(57) ABSTRACT

Disclosed is an HFO-1234ze preparation process. The present invention is realized by loading two fluorination catalysts into the same reactor, and controlling the temperature in each section. The preparation process of the present invention is of moderate reaction condition, stable catalyst activity, and simple process.

11 Claims, No Drawings

1, 3, 3, 3-TETRAFLUOROPROPENE PREPARATION PROCESS

TECHNICAL FIELD

The present invention relates to methods for preparing fluoroalkenes, particularly to a method for the preparation of 1,3,3,3-tetrafluoropropene.

BACKGROUND TECHNOLOGY 1,1,1,3-Tetrafluoropropene (HFO-1234ze) has a lower global warming potential (GWP) and ozone destroying potential (ODP). It is considered a potential substitute for 1,1,1,2-tetrafluoroethane (HFC-134a) and the like uses in forming agent, coolant, and aerosol propellant industries. In addition, HFO-1234ze is a good cleaning agent, for use in cleaning large-scale production equipment. HFO-1234ze is also used as a monomer for the synthesis of thermal stable, high elastic rubber materials; it is an important intermediate materials.

Currently, known methods for the preparation of HFO-1234ze include: using HFC-245fa or CFC-244fa as a starting material in a de-hydrohalogenation reaction to synthesize HFO-1234ze; using HCFC-1233zd as a starting material to first synthesize HFC-245fa and HCFC-244fa by fluorination, famed by de-hydrohalogenation to synthesize HFO-1234ze; and using HCC-240fa as a starting material to first synthesize HCFC-1233zd by fluorination, followed by further fluorination to synthesize HFO-1234ze.

U.S. Pat. No. 6,548,719, Chinese patent No. CN 1852880, PCT publication WO2008147825, etc. disclose methods using a strong alkali to dehydrofluorinate HFC-245fa in a liquid phase to produce HFO-1234ze.

Patent literatures, JP 11140002, U.S. Pat. Nos. 6,124,510, 5,986,151, CN 1852880, CN 1014666656, U.S. 2009/0118555, etc. disclose methods that uses catalysts to dehydrofluorinate HFC-245fa in the gas phase to produce HFO-1234ze.

Patent literatures, U.S. 2005/0020862, U.S. Pat. No. 4,086,407, CN 101032690A, CN 101772480A, etc. disclose methods using catalysts on carbon carrier to dehydrofluorinate HCFC-244fa to produce HFO-1234ze.

Patent literatures, CN1852880, US20050020862, U.S. Pat. No. 7592494, etc. disclose methods using HCFC-1233zd as a starting material, under the action of a catalyst, to synthesize HFC-245fa and HCFC-244fa by fluorination, and then under the action of a strong alkali, dehydrohalogenate HFC-245fa and HCFC-244fa to produce HFO-1234ze.

In the above described methods for the preparation of HFO-1234ze, HFC-245fa is expensive, HCFC-1233zd is difficult to obtain, dehydrofluorination with a strong alkali in a liquid phase will produce large volumes of liquid wastes, and the supported catalysts used in gas-phase dehydrohalogenation reaction do not have long service lives. These methods are not suitable for large scale industrial uses.

Chinese Patent publication CN101028992 discloses a method using HCC-240fa as a starting material to prepare HFO-1234ze using gas-phase catalytic fluorination. This method uses two reactors to carry out the reactions in two steps. The intermediate from the first reaction needs to be purified by distillation before use in the second reaction. The process is complicated and uses a lot of energy. It is not a reasonable use of the resource. If the two steps are carried out in a single reactor, and the reaction temperature is too high, HCC-240fa tends to polymerize and carbonize. If the reaction temperature is low, HFO-1234ze selectivity would decrease.

SUMMARY OF THE INVENTION

The present invention is to provide methods for the preparation of HFO-1234ze that have mild reaction conditions, simple processes and are suitable for large-scale industrial production.

Inventors of the present invention discovered that using HCC-240fa as a starting material and gas-phase fluorination as a process to prepare HFO-1234ze involves two stages: In the first stage, HCC-240fa and/or HCO-1230za are used as starting materials to prepare HCFC-1233zd, and in the second stage, HCFC-1233zd is used to prepare HFO-1234ze. According to this synthetic scheme to synthesize HFO-1234ze, if one temperature is used in a reactor and the temperature is too high, the starting material may polymerize. As a result, the by-products will increase and the service life of the catalyst would decrease. If the reaction temperature is too low, the second stage reaction cannot proceed smoothly and the selectivity for HFO-1234ze would be reduced. Therefore, separate temperature control of the catalysts is the key to prepare HFO-1234ze. Inventors of the present invention chose to heat the catalysts in the reactor to two different temperatures: the temperature in the first stage facilitates the production of HCFC-1233zd, and the temperature at the second stage facilitates the production of HFO-1234ze.

The present invention provides the following technical solutions.

A process for preparing HFO-1234ze, characterized in that the method comprises the following steps:

(1) charging a reactor with a fluorination catalyst in two sections, wherein the first section of the fluorination catalyst is controlled at a temperature of 200-300° C., and the second section of the fluorination catalyst is controlled at a temperature of 350-450° C.; and (2) introducing gasified HF together with HCC-240fa and/or HCO-1230za ($CCl_2$=$CHCHCl_2$) into the reactor, passing through the first section of the fluorination catalyst and then through the second section of the fluorination catalyst, wherein a molar ratio of HF to the total organic phase is from 5:1 to 20:1, a contact time for the reaction is 1-30 seconds, a reaction pressure is 0.1-1.2 MPa, a product stream thus formed is treated to remove acid and remove water, and then distilled to afford HFO-1234ze.

The above-mentioned total amount of organic phase refers to the sum of HCC-240fa and/or HCO-1230za added to the reactor, and the portion of the organic products circulated back into the reactor (including HCFC-1233zd, HFC-245fa, etc.).

During the reaction, the temperatures of the two sections of catalysts are separately controlled. The temperature in the first section cannot be too low. Otherwise, HCC-240fa conversion rate would be low, resulting in a composition in the second section containing increased HCC-240fa and reduced HCFC-1233zd. This will affect the conversion of HCFC-1233zd into HFO-1234ze in the second stage. If the temperature in the first section is too high, carbon deposition on the surface of the catalysts would be accelerated, leading to quick in activation of the catalysts.

For the second stage reaction, if the temperature is too low, selectivity for HFO-1234ze would be reduced. If the temperature is too high, the side reaction will increase. Therefore, in accordance with embodiments of the invention, suitable temperatures are: the temperature for the first section (or first stage) is 200-300° C., and the temperature for the second section (or second stage) is 350-450° C. Preferably, the temperature for the first section (or first stage) is 200-250° C., and the temperature for the second section (or second stage) is 350-400° C.

In accordance with methods of the invention, in step (2) the product stream is preferably processed by distillation. The product stream is introduced into a distillation tower, wherein the operation pressure is 0.1-0.6 MPa. The temperature at the top of the distillation tower is −30-10° C., and the temperature at the pot of the distillation tower is 40-80° C. A stream of HFO-1234ze and HCl is formed at the top of the distillation tower, which after treatments to remove acid and water is distilled to produce HFO-1234ze. In the pot of the distillation tower, a stream containing HCFC-1233zd, HFC-245fa and HF is formed. In a preferred method, the stream containing HCFC-1233zd, HFC-245fa and HF formed in the distillation pot is circulated back into the reactor, thereby shifting the balance of the reaction to the left and suppressing further fluorination of HFO-1234ze to produce HFC-245fa, thereby increasing the selectivity for HFO-1234ze.

In accordance with embodiments of the invention, excess HF can suppress degradation of HCC-240fa in the organic phase, slow down the inactivation of the catalyst, and extend the service life of the catalyst. However, if the molar ratio of HF in the organic phase is too high, under the condition of the same gas flow speed, it will not only reduce the reaction yield per unit time and space, but also will further fluorinate HFO-1234ze to produce HFC-245fa. Therefore, in accordance with embodiments of the invention, the molar ration of HF to the organic phase is preferably 5:1 to 20:1, more preferably 10:1 to 15:1.

In accordance with embodiments of the invention, the longer the reaction contact time, the higher the catalytic activities. However, the yield per unit time and space for the catalyst substantially decreases. Therefore, in accordance with embodiments of the invention, the reaction contact time is preferably 1-30 seconds, more preferably 5-10 seconds.

In accordance with embodiments of the invention, reaction pressure is also an important factor affecting the yield. Increasing reaction pressure does not favor the formation of HFO-1234ze. However, increased reaction pressure can suppress the degradation of HCC-240fa and carbon deposition on the catalyst, thereby extending the life of the catalyst, and facilitate the separation of the reaction products. Therefore, In accordance with embodiments of the invention, the reaction pressure is preferably 0.1-1.2 MPa, more preferably 0.3-0.6 MPa.

Inventors of the present invention also discovered that if oxygen and/or chlorine is introduced into the reactor with the starting material, the service life of the catalyst can be extended. The amounts of the oxygen and/or chlorine to be introduced are preferably selected such that the molar ratio of oxygen and/or chlorine to the organic phase is 0.5-1.5%: 1. Introduction of oxygen can use oxygen, air, a mixture of oxygen and air, or a mixture of oxygen and an inert gas.

Fluorination catalysts suitable for use with embodiments of the invention generally include those commonly known in the art. These catalysts include, but are not limited to, aluminum oxide (alumina); aluminum fluoride; aluminum oxofluoride (alumina fluoride); metal oxide on aluminum fluoride; metal oxide on the aluminum oxofluoride; an oxide, fluoride, and oxofluoride of magnesium, zinc, or a mixture of magnesium and zinc or aluminum; lanthanum oxide and lanthanum oxofluoride; an oxide of chromium, chromium fluoride, and cubic chromium trioxide. Preferred catalysts include chromium based fluorination catalysts, which may be prepared by reaction of $Cr_2O_3$ with HF. Preferred chromium based catalysts include transition metal modified chromium oxide or transition metal modified chromium fluoride, wherein the transition metals are selected from magnesium, VII B metals, III B metal, or a combination thereof containing one, two, or three or more of these transition metals. Chromium based fluorination catalysts preferably are activated prior to use, such as activation with HF and nitrogen.

The physical characteristics of the catalysts are not important, and can include spheres, powders, and granules. Even though it is not necessary, these catalysts preferably are treated with HF prior to use. This treatment can convert some of the oxides on the catalysts into fluorides. This pretreatment may be conducted in a suitable fluorination reactor using a catalysts and HF, by passing HF through dry catalysts to partial saturation. This may be accomplished at a selected temperature, such as 200-500 C, by passing anhydrous HF through catalyst for 15-400 minutes.

In accordance with embodiments of the invention, reactors, distillation towers, and other related material delivery pipes, discharge pipes, and other related units should be made of corrosion resistant materials. Typical corrosion resistant materials include stainless steel and copper plated steel.

The chromium based fluorination catalysts for use in the present invention may be prepared according to the methods disclosed in Chinese patent application No. CN200610105441, which is incorporated herein by reference in its entirety.

As compared with prior art, embodiments of the invention have the following advantages: achieving a two-stage reaction in a reactor by controlling the catalysts in different sections at different temperatures. In addition, the reaction temperatures are mild, the activities of the catalysts are stable; and these methods are simple, etc.

EXAMPLES

The invention will be further explained using the following examples. However, the scope of protection of the present invention is not limited by these examples. One skilled in the art should appreciate that the scope of the invention covers all possible embodiments in the claims, improved embodiments and equivalents thereof.

Example 1

Preparation of Catalysts

Prepare a solution of a soluble salt of Cr, Zn, or Ce (e.g., nitrate, sulfate, chloride etc.) at a selected concentration. At a temperature of 20-100° C., react this solution with a precipitant (NaOH, KOH, $(NH_4)_2CO_3$, ammonia etc.). Control the final pH between 6.5 and 9.5. Mix vigorously to cause the active compositions to completely precipitate. Then, filter the precipitates and wash with deionized water until pH neutral. The filter cake is dried at a temperature of 100-200° C. to produce amorphous catalysts precursors having a specific surface area greater than 200 $m^2/g$, and a porosity greater than 0.3 ml/g.

Add graphite to the catalyst precursors and press the mixture into tablets. Place the tablets into a reactor and calcinated at 200-400° C. under nitrogen atmosphere. Then, pass a mixture of nitrogen and HF to fluorinate the catalysts at 200-400° C. to produce the fluorination catalysts.

Example 2

Preparation of HFO-1234ze

Place a catalyst from Example 1 in a Monel alloy tube (diameter 25 mm; Ø25 mm) The catalyst is after the treatment described in Example 1, and the loading is 50 ml. The catalyst is packed in two equal sections; each has a separate reaction temperature control. The upper section catalyst in the reactor is controlled at a temperature of 250° C., and the lower section catalyst in the reactor is controlled at a temperature of 400° C. After preheating, a mixture of HF and HCC-240fa is introduced into the alloy tube. The molar ratio of HF to CC-240fa is 10:1. The contact time is 5 seconds. The reaction pressure is ambient pressure. After reaction for 20 hours, the reaction product is washed with water, followed by washing with alkali to remove HF and HCl. The product is analyzed with gas chromatography for the rate of conversion of HCC-240fa and the selectivity of HFO-1234ze. The results are shown in Table 1.

Example 3

Preparation of HFO-1234ze

The preparation is the same as in Example 2. The only difference is that the upper section reaction temperature is 200° C. The reaction results are shown in Table 1.

Example 4

Preparation of HFO-1234ze

The preparation is the same as in Example 2. The only difference is that the upper section reaction temperature is 300° C. The reaction results are shown in Table 1.

Example 5

Preparation of HFO-1234ze

The preparation is the same as in Example 2. The only difference is that the lower section reaction temperature is 350° C. The reaction results are shown in Table 1.

Example 6

Preparation of HFO-1234ze

The preparation is the same as in Example 2. The only difference is that the lower section reaction temperature is 450° C. The reaction results are shown in Table 1.

Example 7

Preparation of HFO-1234ze

The preparation is the same as in Example 2. The only difference is that the molar ratio of HF to HCC-240fa is changed to 5:1. The reaction results are shown in Table 2.

Example 8

Preparation of HFO-1234ze

The preparation is the same as in Example 2. The only difference is that the molar ratio of HF to HCC-240fa is changed to 20:1. The reaction results are shown in Table 2.

TABLE 2

| Example | Molar Ratio | HCC-240fa Conversion rate/% | Selectivity/% HCFC-1233zd | Selectivity/% HFO-1234ze | Selectivity/% HFC-245fa |
|---|---|---|---|---|---|
| 2 | 10:1 | 97.5 | 35.7 | 45.1 | 19.2 |
| 7 | 5:1 | 95.1 | 50.8 | 40.0 | 9.2 |
| 8 | 20:1 | 98 | 38.1 | 33.6 | 28.3 |

Example 9

Preparation of HFO-1234ze

The preparation is the same as in Example 2. The only difference is that the reaction contact time is changed to 10 seconds. The reaction results are shown in Table 3.

Example 10

Preparation of HFO-1234ze

The preparation is the same as in Example 2. The only difference is that the reaction contact time is changed to 20 seconds. The reaction results are shown in Table 3.

TABLE 3

| Example | Contact Time (s) | HCC-240fa Conversion rate/% | Selectivity/% HCFC-1233zd | Selectivity/% HFO-1234ze | Selectivity/% HFC-245fa |
|---|---|---|---|---|---|
| 2 | 5 | 97.5 | 35.7 | 45.1 | 19.2 |
| 9 | 10 | 100 | 32.5 | 42.9 | 24.6 |
| 10 | 20 | 100 | 30.6 | 36.0 | 33.4 |

TABLE 1

| Example | Upper Section Reaction Temp./° C. | Lower Section Reaction Temp./° C. | HCC-240fa Conversion rate/% | Selectivity/% HCFC-1233zd | Selectivity/% HFO-1234ze | Selectivity/% HFC-245fa |
|---|---|---|---|---|---|---|
| 2 | 250 | 400 | 97.5 | 35.7 | 45.1 | 19.2 |
| 3 | 200 | 400 | 96.2 | 40.6 | 50.3 | 9.1 |
| 4 | 300 | 400 | 99.4 | 39.2 | 45.5 | 15.3 |
| 5 | 250 | 350 | 95.2 | 30.3 | 30.4 | 39.3 |
| 6 | 250 | 450 | 97.7 | 30.5 | 54.2 | 15.3 |

Example 11

Preparation of HFO-1234ze

Place a catalyst from Example 1 in a Monel alloy tube (diameter 25 mm; Ø25 mm). The catalyst is after the treatment described in Example 1, and the loading is 400 ml. The catalyst is packed in two equal sections; each has a separate reaction temperature control. The upper section catalyst in the reactor is controlled at a temperature of 250° C., and the lower section catalyst in the reactor is controlled at a temperature of 400° C. After preheating, a mixture of HF and HCC-240fa is introduced into the reactor to react. The molar ratio of HF to CC-240fa is 10:1. The contact time is 5 seconds. The reaction pressure is 0.35 MPa. The reaction product is flowed into a distillation tower. The distillation tower has an operation pressure of 0.3 Mpa. The temperature at the top of the distillation tower is 10 C, and the temperature in the pot of the distillation tower is 70 C. A product stream containing HFO-1234ze and HCl is formed at the top of the distillation tower. After washing with alkali to remove HF and HCl, the product stream is distilled to produce HFO-1234ze. In the pot of the distillation tower, a material stream containing HCFC-1233zd, HFC-245fa 和 HF is formed, which is circulated back into the reactor. Material compositions at the reactor outlet, distillation tower top, and the pot of the distillation tower are shown in Table 4.

TABLE 4

| Material Composition | Material stream at reactor outlet | Top of distillation tower | Pot of distillation tower |
|---|---|---|---|
| HCC-240fa/Mol % | 0.3 | / | 1.1 |
| HCFC-1233zd/Mol % | 4.3 | / | 5.8 |
| HFC-245fa/Mol % | 2.1 | / | 3.2 |
| HFO-1234ze/Mol % | 5.2 | 51.8 | / |
| HCl/Mol % | 4.8 | 48.2 | / |
| HF/Mol % | 83.3 | / | 89.9 |

What is claimed is:

1. A method for preparing 1,1,3-Tetrafluorontopene (HFO-1234ze), characterized in that the method comprises the following steps:
   (1) charging a reactor with a fluorination catalyst in two sections, wherein the first section of the fluorination catalyst is controlled at a temperature of 200-300° C., and the second section of the fluorination catalyst is controlled at a temperature of 350-450° C.; and
   (2) introducing a gasified HF with 1,1,1,3,3-pentachloropropane (HCC-240fa) and/or 1,1,3,3-tetrachloro-prop-1-ene (HCO-1230za) into the reactor, passing through the first section of the fluorination catalyst and then through the second section of the fluorination catalyst, wherein a molar ratio of HF to the total organic phase is from 5:1 to 20:1, a contact time for the reaction is 1-30 seconds, and a reaction pressure is 0.1-1.2 MPa, forming a product stream; and
   (3) passing the product stream through a distillation tower;

wherein:
   a stream containing HFO-1234ze and HCl is formed at the top of the distillation tower and the stream is further treated to remove acid and water and distilled to produce HFO-1234ze;
   a material stream containing 1-chloro-3,3,3-trifluoropropene (HCFC-1233zd), 1,1,1,3,3-pentafluoropropane(HFC-245fa) and HF is formed in a pot at the bottom of the distillation tower; and
   the pressure in the distillation tower is 0.1-0.6 MPa, a temperature at the top of the tower is −30-10° C. and the temperature in the pot at the bottom of the distillation tower 40-80° C.

2. The method for preparing HFO-1234ze according to claim 1, characterized in that the material stream containing HCFC-1233zd, HFC-245fa and HF is circulated back into the reactor.

3. The method for preparing HFO-1234ze according to claim 1, characterized in that the first section of the fluorination catalyst is controlled at a temperature of 200-250° C. and the second section of the fluorination catalyst is controlled at a temperature of 350-400° C.

4. The method for preparing HFO-1234ze according to claim 1, wherein in step (2), the molar ratio of HF to the total organic phase is from 5:1 to 20:1, the contact time for the reaction is 5-10 seconds, and the reaction pressure is 0.3-0.6 MPa.

5. The method for preparing HFO-1234ze according to claim 4, wherein the molar ratio of HF to the total organic phase is from 10:1 to 15:1, the contact time for the reaction is 5-10 seconds, and the reaction pressure is 0.3-0.6 MPa.

6. The method for preparing HFO-1234ze according to claim 1, characterized in that a stream comprising oxygen gas and/or chlorine gas is introduced into the reactor, wherein a molar ratio of the stream comprising oxygen gas and/or chlorine gas to a total amount of organic phase is 0.5%-1.5%:1.

7. The method for preparing HFO-1234ze according to claim 1, characterized in that the fluorination catalyst is a chromium based fluorination catalyst.

8. The method for preparing HFO-1234ze according to claim 7, characterized in that the chromium based fluorination catalyst is prepared by reacting $Cr_2O_3$ with HF.

9. The method for preparing HFO-1234ze according to claim 7, characterized in that the chromium based fluorination catalyst is a transition metal modified chromium oxide or a transition metal modified chromium oxofluoride, wherein the transition metal is selected from the group consisting of magnesium, group VIIB metal, group IIIB metal, zinc, and a mixture thereof.

10. The method for preparing HFO-1234ze according to claim 7, characterized in that the chromium based fluorination catalyst is activated prior to use.

11. The method for preparing HFO-1234ze according to claim 10, characterized in that the chromium based fluorination catalyst is activated by treatment with HF and nitrogen gas prior to use.

* * * * *

UNITED STATES PATENT AND TRADEMARK OFFICE
CERTIFICATE OF CORRECTION

PATENT NO. : 9,458,070 B2
APPLICATION NO. : 14/653510
DATED : October 4, 2016
INVENTOR(S) : Lei Xu et al.

Page 1 of 1

It is certified that error appears in the above-identified patent and that said Letters Patent is hereby corrected as shown below:

In the Claims

Claim 1, Column 7, Line Number 41, "1,1,3-Tetrafluorontopene" should read
-- 1,3,3,3-Tetrafluoropropene --.

Signed and Sealed this
Twenty-seventh Day of March, 2018

Andrei Iancu
*Director of the United States Patent and Trademark Office*